United States Patent [19]

Gibboney et al.

[11] Patent Number: 4,912,417

[45] Date of Patent: Mar. 27, 1990

[54] MEASUREMENT OF PH AND SPECIFIC ION CONCENTRATION

[75] Inventors: Dennis A. Gibboney, Mount Pleasant; Frank R. Frola, North Huntington; Dominick Frollini, Jr., Trafford; John T. Schneider, Washington Township, Westmoreland County, all of Pa.

[73] Assignee: Fisher Scientific Company, Pittsburgh, Pa.

[21] Appl. No.: 313,070

[22] Filed: Feb. 21, 1989

[51] Int. Cl.$^4$ ............................................. G01N 27/46
[52] U.S. Cl. ..................................... 324/438; 364/497; 204/406; 204/407; 204/408; 204/400
[58] Field of Search ............... 204/1 H, 401, 400, 406, 204/407, 408; 364/497; 73/1 R; 324/464, 453, 438; 422/98

[56] References Cited

U.S. PATENT DOCUMENTS

| | | | |
|---|---|---|---|
| 4,353,867 | 10/1982 | Luzzana | 204/1 H |
| 4,649,028 | 3/1987 | Kaltenbach et al. | 422/100 |
| 4,668,346 | 5/1987 | Entwistle | 204/401 |
| 4,779,446 | 10/1988 | Rowland | 73/1 R |

FOREIGN PATENT DOCUMENTS

| | | | |
|---|---|---|---|
| 2937227 | 9/1982 | Fed. Rep. of Germany. | |
| 3220327 | 12/1982 | Fed. Rep. of Germany | 204/401 |
| 2188435 | 9/1987 | United Kingdom | 204/401 |

OTHER PUBLICATIONS

Corning Science Products, "pH/Ion Meter 135 Instruction Manual" (Cat. No. 477332, Rev. B, 6/79).
Fisher Scientific, "Instructions Fisher Accumet Model 925 Meter" (Rev. A Published Mar., 1987; bulletin 7-1019-n).

Primary Examiner—Reinhard J. Eisenzopf
Assistant Examiner—Jose M. Solis
Attorney, Agent, or Firm—Alan M. Doernberg

[57] ABSTRACT

A microprocessor-controlled pH and ion concentration meter is disclosed with improved calibration and testing procedures. For calibration (standardization), the meter stores number pairs $(pX_a, E_a)$, $(pX^b, E_b)$ where the pX values may be pH values (e.g., 4.00 and 7.00) and the E values are expressed in mV/deg K. When multiple standard values are stored, remeasuring one (e.g., replacing $E_{a1}$ by $E_{a2}$) can be used to update the others (e.g., $E_{b1}$ to $E_{b2}$) without remeasurement by applying the formula:

$$E_{b2} = E_{b1} + (E_{a2} - E_{a1}).$$

Additionally, the meter can be tested for excessive internal bias current by measuring the potential (V1) when the meter is connected to a circuit of low impedance and the potential (V2) when the meter is connected to a circuit of the same voltage source but of known high impedance and having the meter compare (V2−V1) to a preset limit value.

16 Claims, 9 Drawing Sheets

MEASUREMENT OF PH AND SPECIFIC ION CONCENTRATION

The present invention relates to measuring pH and specific ion concentrations potentiometrically, and especially to meters for use in combination with electrodes for such measurement.

Electrodes for measuring hydronium (pH) and other ions such as alkali metal, ammonium or alkaline earth metal cations or halide or sulfide anions are well known. Typically, the electrodes are first connected electrically to a meter which serves to measure the potential difference between the indicating electrode and the reference electrode. The indicating and reference electrodes, separately or in combination form, are then immersed in the unknown solution. The meter converts the measured electrical potential to a calculated and displayed value referred to as pX (pH in the case of hydronium cations). For ions other than hydronium, a concentration value (in units such as ppm) is calculated from the exponent pX and displayed.

Various problems are encountered in the testing and operation of the meter. These problems include: (1) ensuring that the input bias current (of the input operational amplifier of the meter) is sufficiently low to have no significant effect upon the measured electrical potential, (2) efficiently recalibrating the meter to correct for drift in electrode output potential and (3) establishing when the measured electrical potential (whether from a test circuit or an electrode input) is acceptably stable. Each of these operations has often led to excessive manual operations by the meter manufacturer or by the user.

In determining whether the internally-generated voltage of the meter is a cause for excessive error, either at the time of manufacture or after use, it has been possible to connect the meter to a test circuit having additional resistance (generally much larger than the resistance of the electrode in use), a difference in measured voltage can be obtained. Traditionally, this difference has been converted by external calculation to a value for bias current. This bias current value can be used to estimate the pX or pH error that results from the high impedance of the measuring electrode. An example of such a computation is shown below:

$$PH_{error} = \text{Slope(units/volts)} * R_{electrode} * I_{bias}$$

anf for a typical electrode at 25 deg C.

$$pH_{error} = 17 * 10^8 * I_{bias}$$

where $I_{bias}$ is computed as:

$$I_{bias} = \frac{V_{no\ resistor} - V_{with\ 5\ G\ resistor}}{5 * 10^9}$$

The difficulty in this procedure is that it requires both multiple manual manipulations and a calculation which, even if automated, must employ a calculating device external to the meter.

In the case of calibration, it is common to measure the electrode output potential in two or more solutions of known pX (sometimes after automatic compensation for temperature). For best accuracy, sample voltages are converted to pX values based upon measured values for two standards, one of lower pX and one of higher pX. Moreover, it is desirable that at least one of two standards have a pX similar in value to that of the standard. To mutually satisfy these criteria (known as "bracketing"), frequently at least three standards are used. While the three values can be stored and each unknown calculated from the two stored values on either side, over time the system will drift and require recalibration. Conventionally, all three standards are measured again to develope a new calibration value. This is time consuming and labor intensive since the electrodes must be washed between immersion into each standard and permitted time to equilibrate in the standard.

In biological fields such as blood gas measurement, recalibration of less than all of the standards (one of two before each measurement in blood gas) has been employed If, however, one updates only the remeasured value, the effect will be to change the slope of the voltage to pX curve (see FIG. 5). Unfortunately, if the criteria for close bracketing of sample values by standards is met, it may be seen that the error associated with drift in the curve displacement with time greatly exceeds that caused by drift in slope.

Finally, whether connected to electrodes or to the external circuit for testing, the meter measures an input voltage which varies over time. This variation is steep initially, typically asymptotically approaching a final value within 10–30 seconds for pH electrodes. This interval is often much longer for other electrode types, e.g., gas sensors such as carbon dioxide or ammonia electrodes. Some meters are commercially designed to wait a fixed period before taking a measurement of voltage from which a standardization value is taken or a pX is calculated. Others take a running average of values at fixed intervals and display that average. Meters with multiple resolution settings have been employed which wait different fixed periods of time after first reading depending upon the resolution selected (e.g., 4 seconds for a resolution of 0.1 pH units, 8 seconds for a resolution of 0.01 pH units and 16 seconds for a resolution of 0.001 pH units). Any such method based upon time alone fails to recognize differences in basic design, sample history and environment among electrode pairs or differences between test circuits and electrode pair circuits. Any such method which compares the running average to latest value with a fixed criterion ignores the relevance of resolution: it may wait too long in low resolution settings and measure too soon for high resolution settings.

The field of meters for pH and pX electrodes has also undergone trends towards minaturization, increased offering of automated features and incorporation of more modern electronic components.

BRIEF DESCRIPTION OF THE INVENTION

The present invention provides meter devices and methods which accomplish one or more of the testing, calibration and measuring functions described above in an improved fashion. The improvements minimize manual operations, reduce time and expertise required for meter testing during production and reduce user time spent calibrating the system in use.

In one form, the present invention provides a method for measuring pX values in unknown solutions with calibration comprising the steps:

(a) measuring the voltage output of an electrode pair in a first solution of known pX value ($pX_a$) and storing this value as $E_{a1}$;

(b) measuring the voltage output of the electrode pair in a second solution of known pX value ($pX_b$) and storing this value as $E_{b1}$;

(c) thereafter measuring the voltage output of the electrode pair in a first solution of unknown pX (pX$_{u1}$) and computing pX$_{u1}$ according to the formula:

$$pX_{u1} = \frac{pX_a*(E_{u1} - E_{b1}) - pX_b*(E_{u1} - E_{a1})}{E_{a1} - E_{b1}}$$

and reporting the computed value of pX$_{u1}$;

(d) thereafter remeasuring the voltage output of the electrode pair in a solution of the first known pX value pX$_a$ and storing the remeasured value E$_{a2}$;

(e) thereafter changing the stored value E$_{b1}$ to a stored value E$_{b2}$ according to the formula:

$$E_{b2} = E_{b1} + (E_{a2} - E_{a1});$$

and (f) thereafter measuring the output voltage E$_{u2}$ of the electrode pair in a second solution of unknown pX and computing pX$_{u2}$ according to the formula:

$$pX_{u2} = \frac{pX_a*(E_{u2} - E_{b2}) - pX_b*(E_{u2} - E_{a2})}{E_{a2} - E_{b2}}$$

and reporting the computed value of pX$_{u2}$.

In a second form, the present invention provides a meter having means for receiving the voltage output of an electrode pair, means for storing standard voltages (E$_{a1}$, E$_{b1}$) from the immersion of the electrode air into standard solutions, means for calculating the pX value of an unknown solution (pX$_{u1}$) from the measured value E$_{u1}$ and the stored standard values, means for updating E$_{a1}$ to E$_{a2}$ by remeasuring the voltage output of an electrode pair in a standard of a first known pX (pX$_a$), means for updating another stored standard voltage (E$_{b1}$ to E$_{b2}$) without remeasurement by the formula:

$$E_{b2} = E_{b1} + (E_{a2} - E_{a1})$$

and means for computing the pX value of a second unknown solution from the measured voltage output of the electrode pair in an unknown solution E$_{u2}$ and from the updated standard values E$_{a2}$ and E$_{b2}$.

In a third form the present invention provides a method for testing a pH or pX meter for excessive internal bias current which comprises the steps:

(a) connecting the electrode inputs of the meter to an external circuit having a known voltage of value E1 and a low external resistance and storing the measured voltage V1, (b) connecting the electrode inputs of the meter to an external circuit having the known voltage E1 and a large known resistance R1 and storing the measured voltage V2, (c) having the meter calculate the value of the difference between V1 and V2, (d) having the meter compare the calculated difference to a permitted range which is preset in the meter and is based upon fixed values of E1 and R1, and (e) if the difference between V1 and V2 is outside the preset limits, having the meter display an error message indicating that the meter is out of specification.

In several forms of the invention, it is preferred that each measuring step performed by the meter (whether of standard solutions, of unknown solutions or of test systems as in steps b and d of the method of the third form) include steps:

(1) taking and storing measured voltage values at fixed intervals (e.g., every one second), (2) calculating the average of the stored set of values, (3) as each additional value is stored beyond a fixed number (e.g., 5), discarding the oldest value and calculating a new average of the set of values, (4) comparing each calculated average to the most recent value stored and determining a difference therebetween, and (5) when the difference is an amount greater than an amount set as the resolution of the meter (or otherwise set as a threshhold) for a fixed time period (e.g., 5 seconds), then repeating (3), (4) and (5), and (6) once the difference is an amount no more than an amount set as the resolution of the meter (or as otherwise set as a threshhold), then storing and/or displaying the latest value or the running average.

DETAILED DESCRIPTION OF THE INVENTION

Various aspects of the invention will be illustrated and explained with reference to the single embodiment of a meter shown in the various Figures at various stages of testing, standardization and use.

Description Of A Preferred Embodiment

Figure 1A:
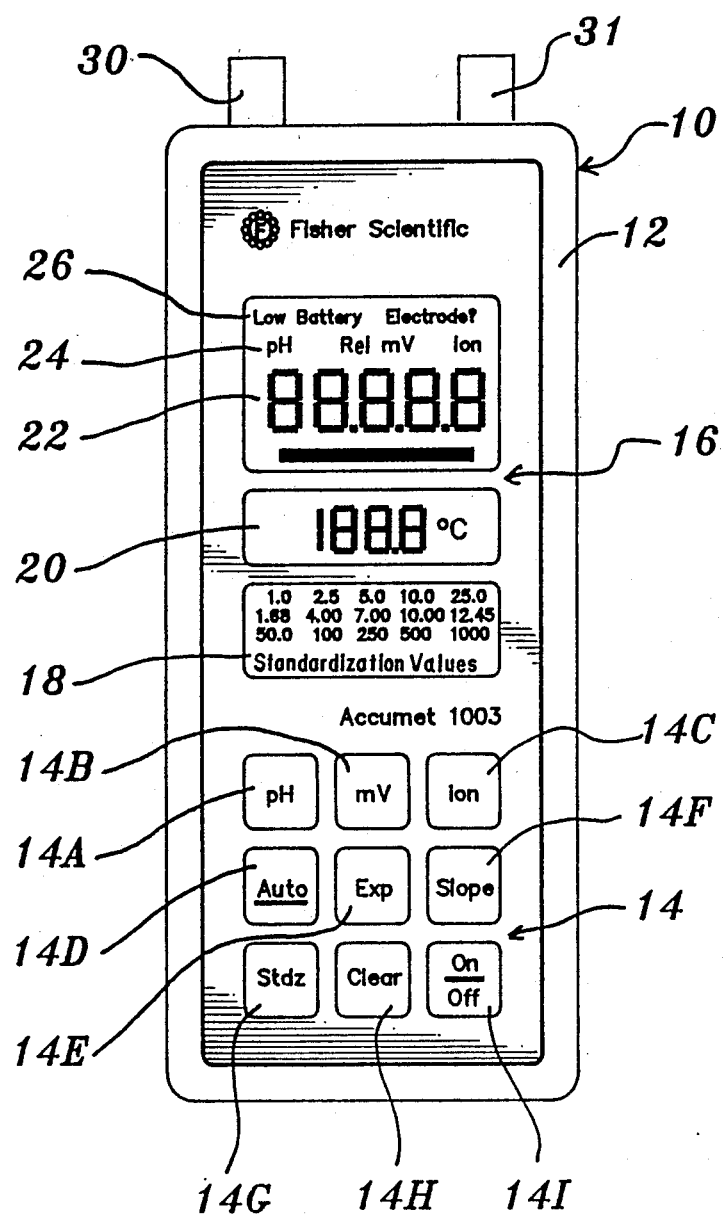
FIG. 1A is a front view of a meter according to an embodiment on the present invention, in a test mode in which all displays are activated.

FIG. 1A illustrates the front of a pH/pX meter 10 according to one embodiment of the present invention. The case 12 of meter 10 covers the exterior of the meter except for a panel containing keypad 14 and a series of display elements designated generally as 16. The keypad 14 includes nine keys 14A through 14I with indicia representing the function of each key as described below. The display 16 includes, moving upward from the keypad 14, a standardization value display 18, a temperature display 20, a value display 22, a display for value type units 24 and a special message display 26. Two jacks 30 (for pH and mV) and 31 (for pX) extend upward through the top of case 12.

The meter 10 is shown in FIG. 1A in a test mode in which all of the liquid crystal elements of display 16 (including all of display components 18, 20, 24 and 26) are activated. FIGS. 3A, 3B, 4A, 4B and 4C, below, indicate examples of the selective activation of various elements of the display 16.

Figure 1B:
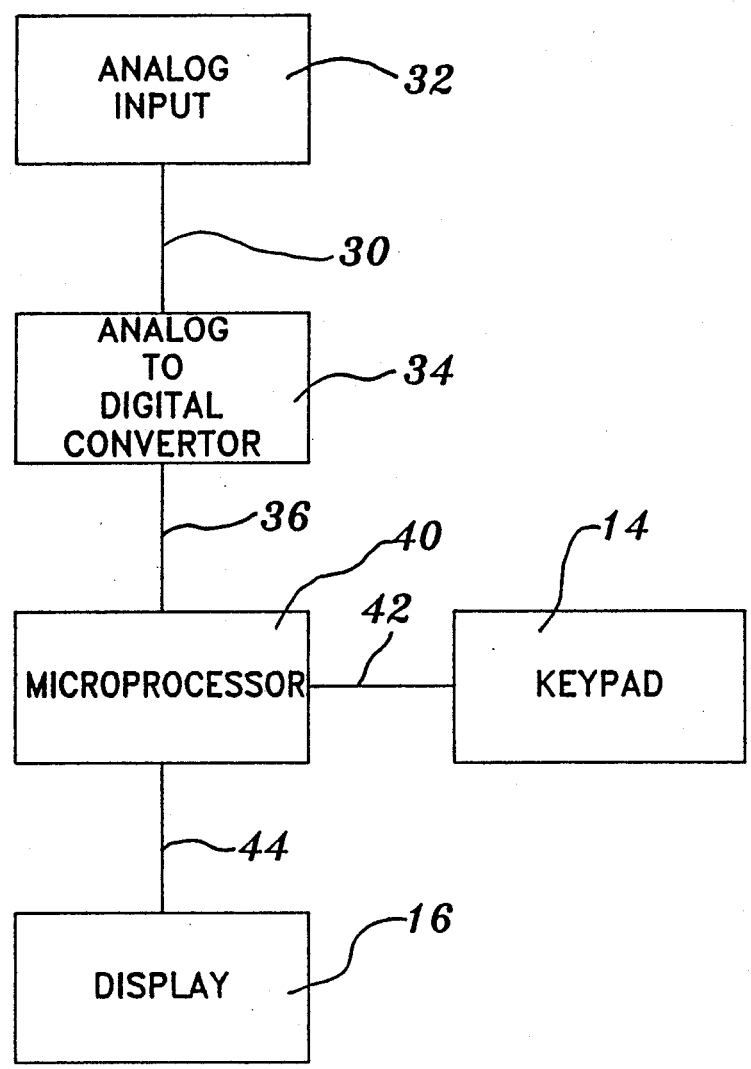
FIG. 1B is a schematic view of the major components of the meter of FIG. 1A connected to an analog input.

FIG. 1B is a schematic rendering of the functional components of meter 10. An analog input 32 (which as described below could be an electrode pair, a combination electrode or a test circuit) is connected via jack 30 to an analog to digital converter device 34, which converts the voltage of analog input 32 into a digital signal 36. That digital signal 36 is a first input into a microprocessor 40, described more fully below in reference to FIG. 1C and contained on a circuit board within case 12 of meter 10. Keypad input 42 represents the connection of the various keys of keypad 14 to microprocessor 40. Output 44 from microprocessor 40 to display 16 is representative of various control lines that connect microprocessor 40 to the individual liquid crystal display elements of the components of display 16.

Figure 2:
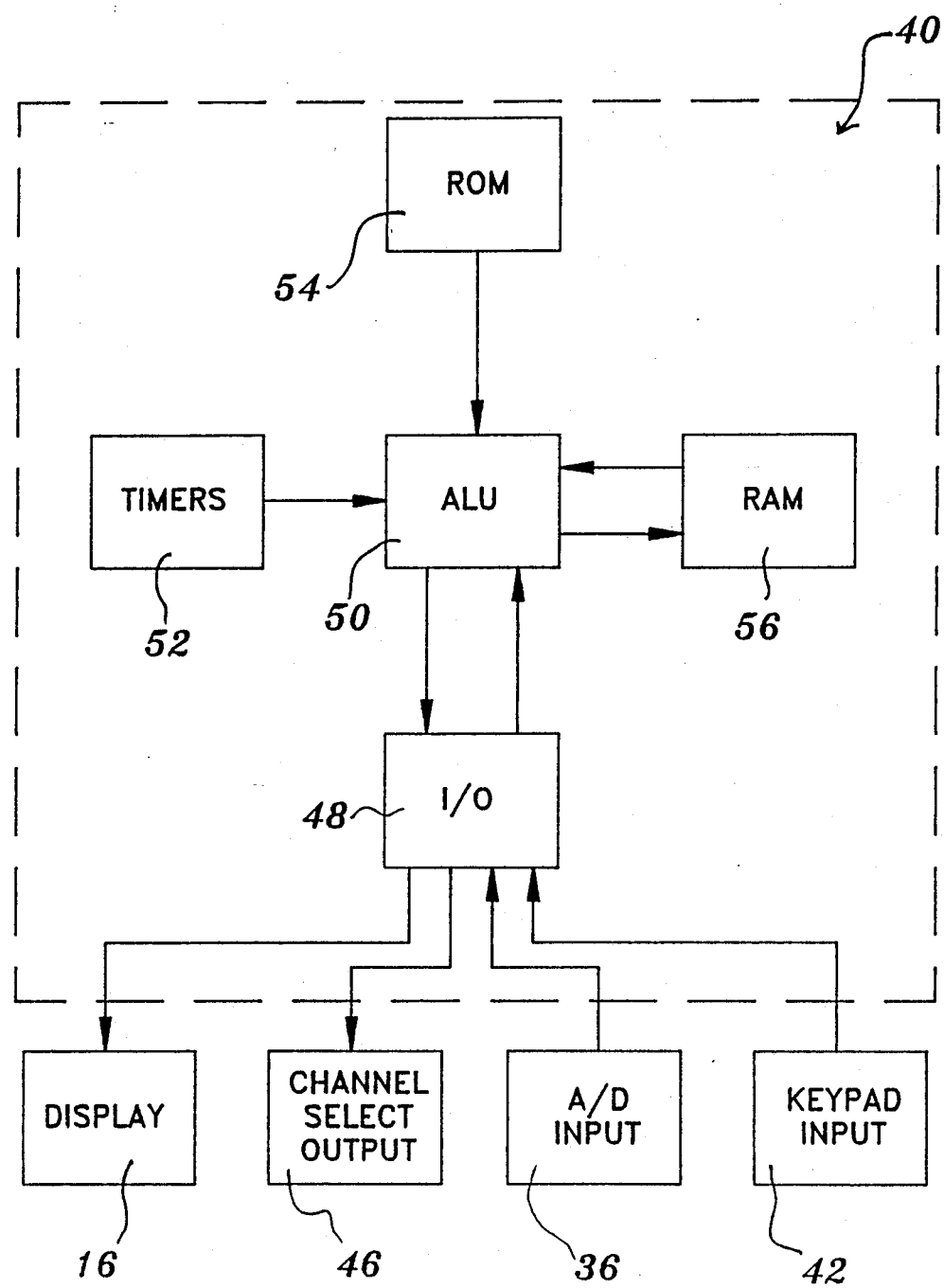
FIG. 2 is a schematic view of the major functional elements of the microprocessor 40 shown in FIG. 1B and its functional connection to other components of the meter.

FIG. 2 illustrates in schematic form the microprocessor 40, its major logic elements and the connecting elements. While microprocessor 40 could be constructed of an assembly of discrete logic devices or transistors, it is preferred to form microprocessor 40 as a custom mask microcomputer chip, such as the M50932-XXXFP chip from Mitsubishi Electric Corporation.

The two types of inputs to the microprocessor 40 are the digitized input 36 (shown as coming from A/D Converter 34 in FIG. 1B) and the keypad input 42 (shown as coming from keypad 14 in FIG. 1B). The two types of outputs from the microprocessor 40 are the display outputs to individual elements of display 16 and the channel selector output 46 which determines whether A/D Converter 34 (see FIG. 1B) is connected to jack 30 or to jack 31 or to the temperature jack between them (see FIG. 1A). FIG. 2 illustrates these two types of inputs and two types of outputs graphically above elements 16, 46, 36 and 42.

The two types of inputs and both types of outputs connect through the I/O interface 48 to the arithmetic logic unit 50 of microprocessor 40. Additional inputs to ALU 50 are timer circuits 52 used (for example) for indicating increments (such as each second) at which ALU performs certain functions. The microprocessor 40 also contains read only memory (ROM) 54 in which various program routines and constants are permanently stored and called up by ALU in a controlled fashion. Random access memory (RAM) 56 contains various values obtained by ALU 48 from I/O 48 or from computations on those values, on stored values already in RAM 56, on values from ROM 54 or on values from a variety of sources.

The operation of the components of the microprocessor 40 shown in FIG. 2 to perform various computations and routines will be described below after the description of the remaining figures.

Figure 3A:
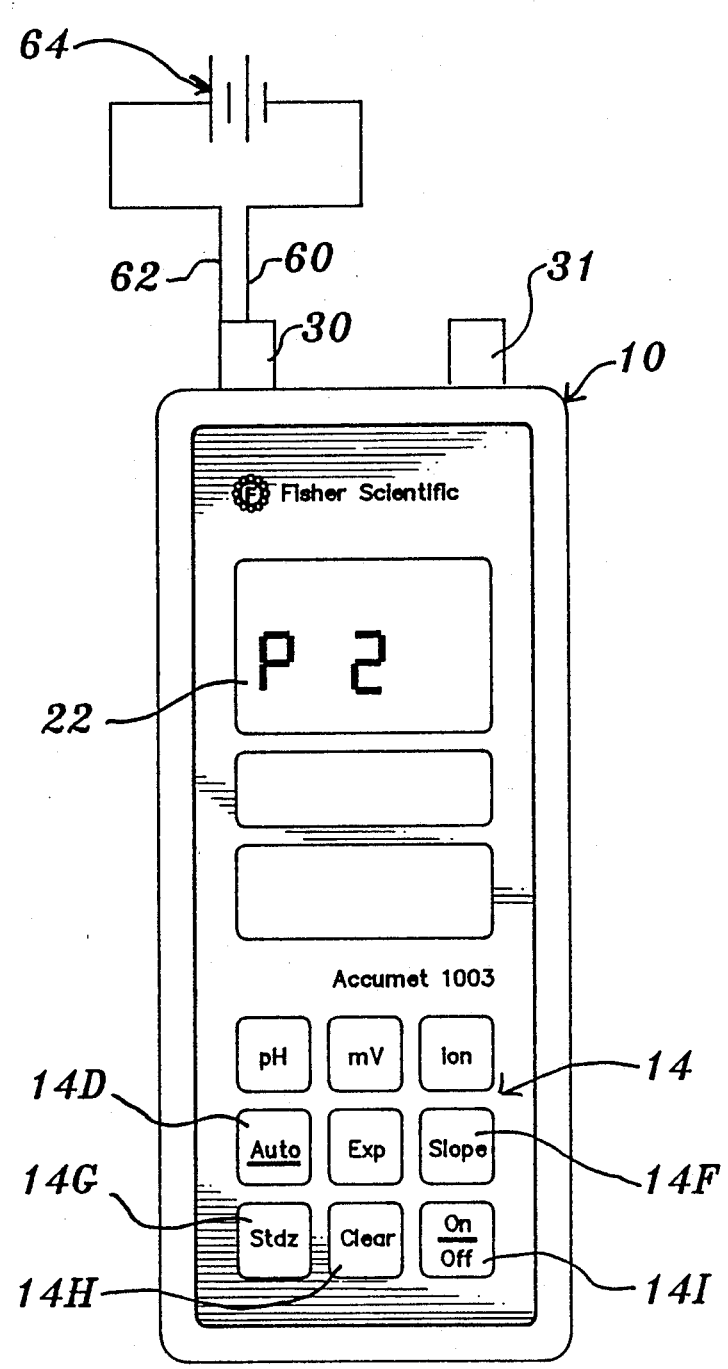
FIG. 3A is a front view of the meter of FIG. 1A connected to a schematically-shown first test circuit.

FIG. 3A shows meter 10 connected to a first test circuit as part of the testing of the internal bias current. A plug is inserted into jack 30 so that line 60 on the plug is connected to the inner contact of jack 30 and line 62 is connected to the outer contact or sleeve of jack 30. Lines 60 and 62 are connected to opposite poles of a battery 64 of known voltage, e.g. 0.475 V. The circuit represented by elements 60, 62 and 64 is of low impedance.

Figure 3B:
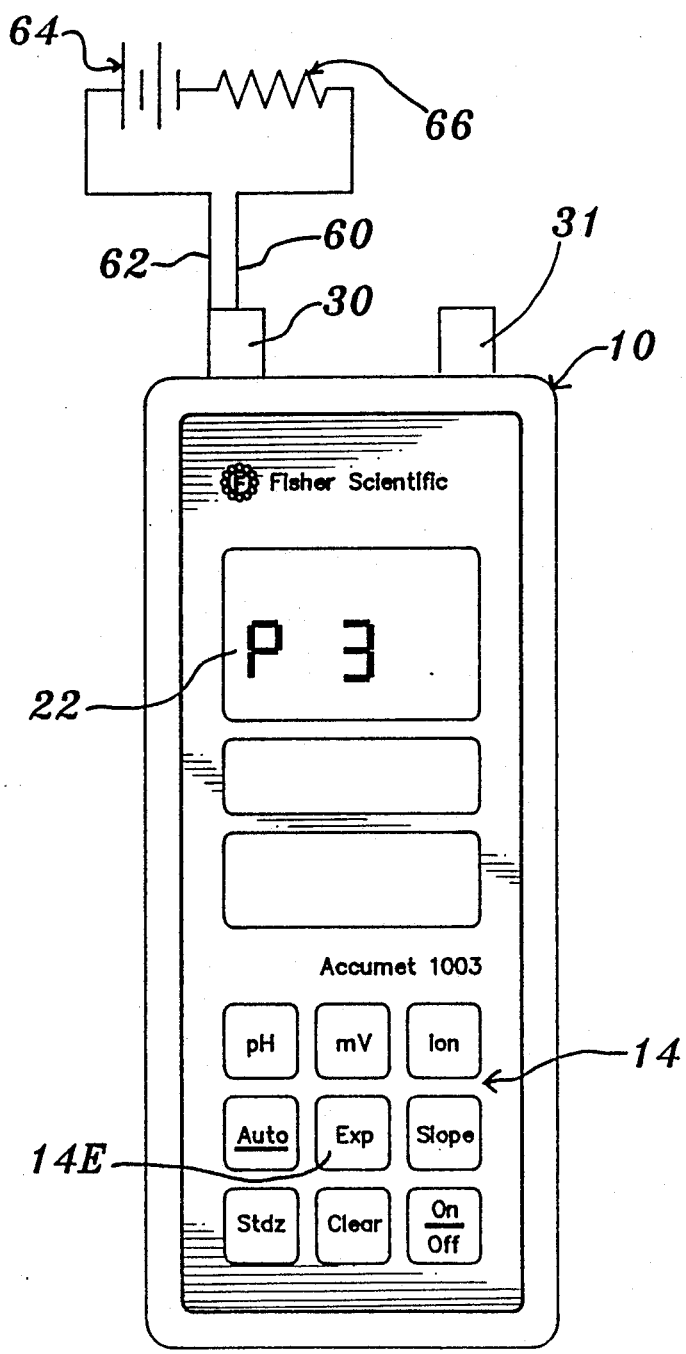
FIG. 3B is a front view of the meter of FIG. 1B connected to a schematically-shown second test circuit.

A person testing the meter in the configuration of FIG. 3A pushes, in order, buttons On/Off 14I, Stdz 14G, Clear 14H, Clear 14H and Slope 14F of keypad 14. Display 22 shows a message ("P2") at this point that indicates to the operator what test circuit to connect to jack 31 (if jack 32 is being tested, it is connected to a similar test circuit). The operator then connects jack 30 to circuit P2 and presses key 14D ("Auto") to initiate testing. The measured voltage for this circuit is then stored (as V1). The meter then indicates at display 22 the next circuit ("P3") to connect to jack 31 (and 32, if being tested). The meter 10 is then connected, as shown in FIG. 3B, to a circuit containing line 60, resistor 66 of high resistance (e.g., $5 \times 10^9$ ohms), battery 64 and line 62. By pushing the Exp key 14E of keypad 14 in this situation, the meter 10 measures the voltage drop between line 62 and line 60 in the circuit of FIG. 3B and stores that value in RAM 56 as V2. V1 is now compared to V2, and the difference is compared to an acceptance limit (for example, 5 mV). If V2−V1 is 5 mV or less, the meter has an acceptable internal bias current (as described below) and passes. If V2−V1 is more than 5 mV, then the internal bias current exceeds specified levels and an error message ("ERR 7") would be displayed on display 22. If the Ion circuit were being tested (by having jack 32 so connected), then if the internal bias current exceeded the specified level, an error message ("Err 8") would be displayed at display 22. If both jacks were connected to test circuits, the meter would test one and then the other and display only that error message which was appropriate. If such bias current testing were part of quality control on a newly assembled meter 10, then either such error message would cause the meter 10 to fail. If such bias testing were part of the evaluation of a meter 10 after a period of use, such an error message would indicate a requirement for repair or replacement.

The selection of an acceptance criterion for V1−V2 is generally fixed in the design of a particular embodiment of the meter. The basis for such a selection is illustrated here. Let it be assumed that one wants meter 10 to have an accuracy of 0.1 mV (approximately 0.002 pH units for most pH electrodes). Then an allowable bias current would be $I = V/R = 10^{-4}$ volts/$10^8$ Ohms $= 10^{-12}$ amps, since a typical pH electrode impedance is about $10^8$ ohms. In the circuit of FIG. 3B, the voltage drop across resistor 66 would correspond to V1−V2 and be:

$$V_{66} = I \times R_{66}$$

and at the maximum permitted level of $I = 10^{-12}$ amps that would be $10^{-12} \times 5 \times 10^9 = 5 \times 10^{-3}$ volts $= 5$ mV. In similar fashion, a permitted internal bias current of $5 * 10^{-12}$ amps would correspond to V1−V2 being 25 mV or less; a permitted internal bias current of $1 * 10^{-11}$ amps would correspond to V1−V2 being 50 mV or less.

It is preferred that the acceptance criterion (in mV for V1−V2) be stored in ROM so that the meter can do a simple comparison. It is less preferred that the meter calculate an actual internal bias current from V1−V2.

The value for $R_{66}$ should be fixed, and should be sufficiently larger than the resistance of any electrode pair that the meter will be used with to give values for V1—V2 much larger than the accuracy of the meter (50 times as great in the example, but preferably at least 10 times as great: e.g., at least $10^9$ ohms for resistor 66 if electrodes of up to $10^8$ ohms are expected).

Figure 4A:
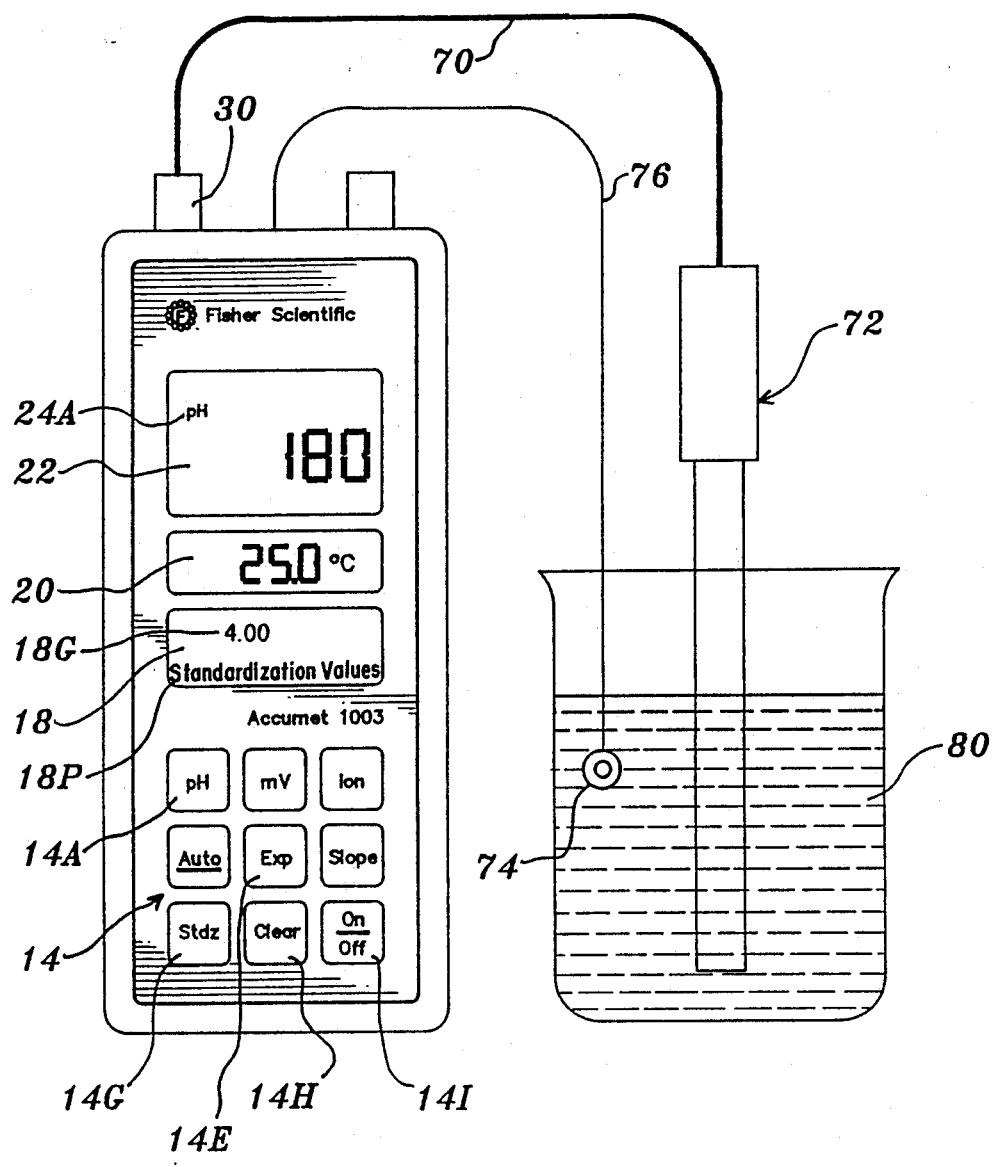
FIG. 4A is a front view of the meter of FIG. 1A connected to a combination pH/reference electrode and to a temperature probe, both immersed in a first standard solution.
Figure 4B:
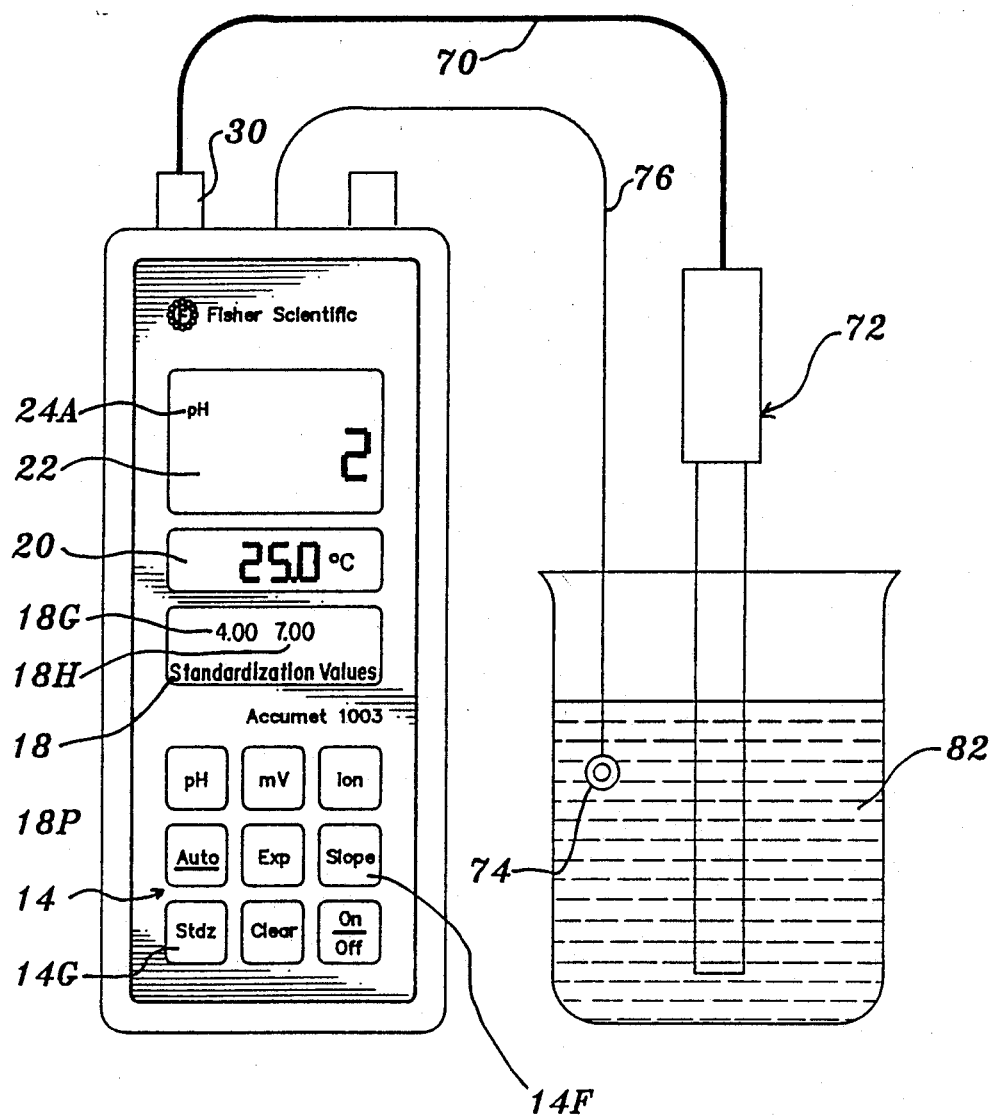
FIG. 4B is a front view of the meter of FIG. 1A connected to a combination pH/reference electrode and to a temperature probe, both immersed in a second standard solution.

After the meter has been thoroughly checked (for conventional features such as mV accuracy, temperature accuracy, input offset voltage, keyboard functionality and display functionality, as well as bias current as described above), it can be activated for one of several measuring modes (pH, pX or mV) and then standardized (especially for pH or pX). FIGS. 4A and 4B are illustrative of intermediate states in the standardization of meter 10 for pH with buffers for pH 4.00 and for pH 7.00 (these values represent the pH of the two buffers at 25 deg C.).

First the meter is turned on by pressing button 14I on keypad 14. The pH mode can then be selected by pressing button 14A. If there are any standardization values already stored, they can be cleared by pressing buttons 14G and 14H successively. Resolution of the display 22 can be adjusted with button 14E (in the pH mode between tenths, hundredths and thousandths of a pH unit; in the Ion mode between two and three significant figures). The location of the decimal in display 22 will indicate in the pH mode which resolution is selected; and the decimal will move between the three positions shown on display 22 in FIG. 1A with each press of key 14E ("EXP" for expansion).

A double cable 70 connects jack 30 with a combination pH/reference electrode 72 which is immersed in a first buffer solution 80. As is conventional, the reference portion of electrode 72 is connected by cable 70 to the exterior or sleeve of jack 30 and the working pH element of electrode 72 is connected by cable 70 to the interior contact of jack 30. Buffer 80 can be any of the NBS standard pH buffers (1.68, 4.00, 7.00, 10.00 or 12.45 at 25 deg C.), but will be illustrated as buffer 4.00.

A temperature probe 74 in buffer 80 is connected by cable 76 to a jack (not shown) extending through the top of housing 12 to the A/D input 36 within meter 10. The temperature sensed by temperature probe 74 is displayed by display 20 and used by ALU 50 in various computations. In general, ALU causes the temperature to be displayed as degrees Celsius, but uses the ratio of mV (at jack 30) divided by degrees Kelvin (at probe 74) for most calculations. To simplify explanations, some of the following discussion will be in terms of millivolts (and thus assume a constant temperature), it being understood that the actual calculations are in millivolts per degree Kelvin. Any absolute scale of temperature having a 0 value at absolute zero can be used (e.g., the Rankine scale which represents degrees F. plus 459.69, just as the Kelvin scale represents degrees C. plus 273.16).

By pushing key 14G with the meter 10 in the pH mode (as indicated at 24A on display 22), the meter 10 takes the signal at jack 30 and searches which (of the five) standardization values it approximates (for the temperature shown at display 20 which is assumed in this example to be 25 deg C. or 298.16 deg K.). While this search is occurring, the words "Standardization Values" at 18P on display 18 flash. Once buffer 80 is recognized as a pH 4.00 buffer, that numeral at 18G on display 18 flashes (the words at 18P now remain displayed). While "4.00" is flashing at 18G, display 22 shows the actual voltage measured at jack 30 (this is the stage actually indicated in FIG. 4A, with 180 millivolts shown on display 22). Once meter 10 has sensed a stabilized value at jack 30 (by the averaging and checking technique described below), the "4.00" displayed at 18G remains on and the numerals "4.00" become displayed at display 22. That value can be displayed as "4.0", "4.00" or "4.000" depending upon the resolution selected with key 14E, which can be changed at any time. If the temperature were not 25 deg C., the value displayed at display 22 would be the pH of buffer 80 at that temperature (e.g., 4.06 at 50 deg C.).

Combination pH/reference electrode 72 can now be removed from buffer 80, as shown in FIG. 4A, rinsed and placed in a second standard buffer 82, as shown in FIG. 4B. It will be assumed that buffer 82 is a pH 7.00 buffer (having that value at 25 deg C.) and that it is at 25 deg at the time of standardization. At this time, display at 24A continues to show that meter 10 is in the pH mode and at 18G continues to show that it has a stored value for pH 4.00. Display 20 shows the temperature sensed by temperature probe 74 (25 deg C.). Depending upon the setting with key 14D (as discussed below), the value displayed at 22 may continue to be "4.00" or may be a different number determined by what is actually measured at jack 30 (using a default value for the slope of the voltage versus pH curve because only one standardization value is retained at this time).

With combination electrode 72 in buffer 82, key 14G is pressed and the words "Standardization Values" at 18P flash as meter 10 determines which standard pH buffer the voltage at jack 30 represents. Once buffer 82 is recognized as 7.00 standard, 18P remains on and "7.00" starts to flash at 18H. While 18H is flashing, display 22 shows the voltage measured at jack 30 in millivolts (2 mV as shown in FIG. 4B). Once that value stabilizes (as discussed below), "7.00" remains on at 18H and the display at 22 becomes "7.0", "7.00" or "7.000", depending upon the display resolution last selected with key 14E.

Figure 4C:
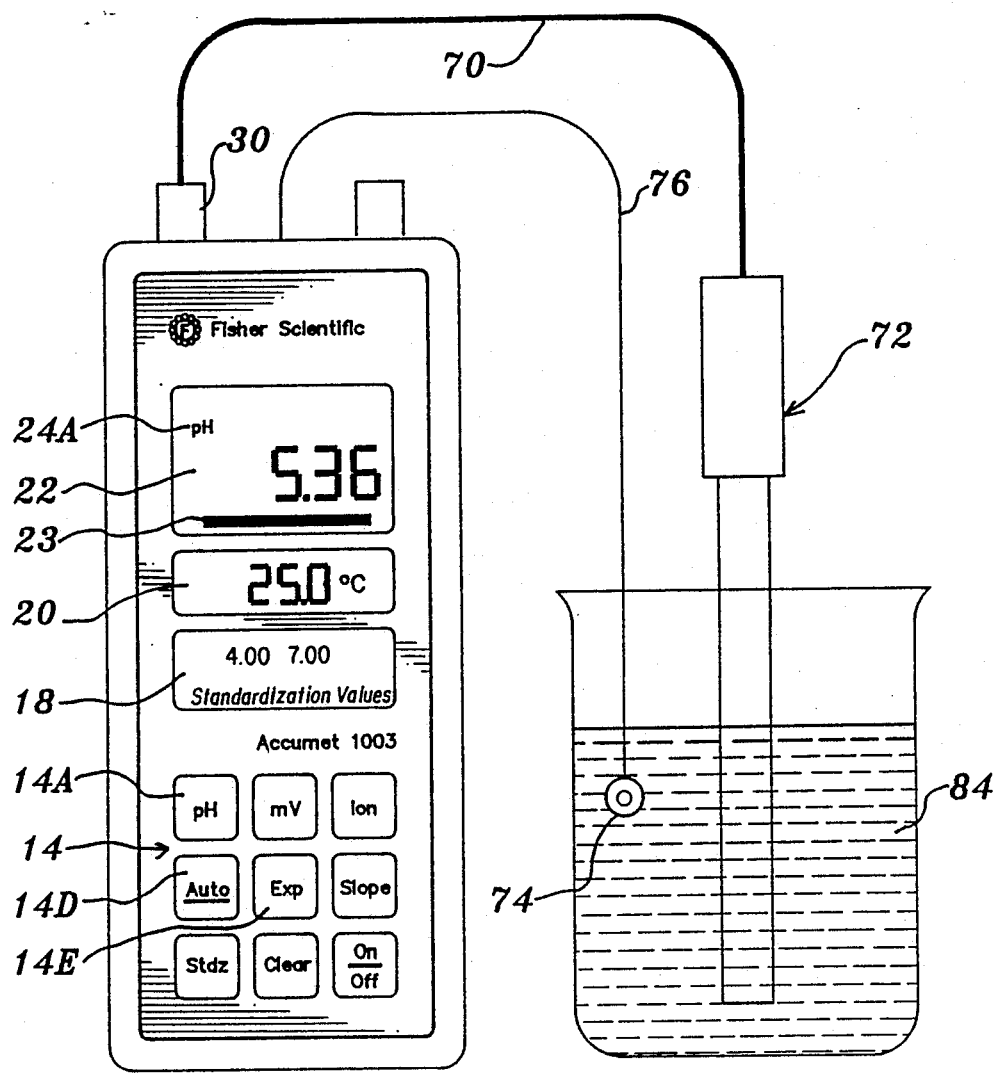
FIG. 4C is a front view of the meter of FIG. 1A connected to a combination pH/reference electrode and to a temperature probe, both immersed in a sample solution of unknown pH.

The electrode 72 can now be rinsed and immersed in a sample solution 84 of unknown pH as shown in FIG. 4C. If key 14D had been used to put meter 10 in a monitor mode (with bar 23 not shown on display 22), then the current pH value calculated from the retained standardization values at 4.00 and 7.00 would be displayed on display 22. Let it be assumed, however, that key 14D has been pressed to activate the Automatic mode. Then, after the pH key 14A has been pressed to initiate an automatic measurement, bar 23 will flash on display 22 while the voltage at jack 30 is rapidly changing (the continuously measured pH value is displayed at display 22 above the flashing bar 23); but the bar 23 will remain on once a constant value is obtained. As described below, in the Automatic mode with a resolution of hundredths of a pH unit selected, the latest voltage converted into pH units must be within 0.005 pH units of the average of the last five voltages (measured every second and converted into pH units in accordance with the retained calibration values) for five seconds before bar 23 stops flashing and before a final pH value is displayed at 22. In this Automatic mode, key 14A must be pressed for bar 23 to resume flashing until a stabilized pH value is obtained, at which time bar 23 stays displayed and the new final pH value is displayed at 22. FIG. 4C shows a displayed pH of 5.36.

In such fashion, pH meter 10 can now be used to measure the pH of multiple samples using the stored standardization values for pH 4.00 and pH 7.00 (actually the stored values of mV/deg K for buffers 80 and 82). A third standardization value can be similarly obtained with a different buffer (1.68, 10.00 or 12.45) and, in conventional fashion, meter 10 will take the voltage of a subsequent sample, determine which two standards are appropriate and convert to pH units using the values for mV/deg K for those two standards and for the sample. If standardization is performed with a fourth buffer (e.g., 1.68) different from the three for which standardizations are stored (e.g., 4.00, 7.00 and 10.00), the furthest standardization (10.00) will be erased from RAM and the three new standardizations (1.68, 4.00 and 7.00) will be stored in RAM and indicated on display 18.

Assume now that meter 10 has stored standardization values as follows:

| pH | mV | mV/deg K |
|---|---|---|
| 4.00 | +180 | 0.604 |
| 7.00 | +2 | 0.007 |
| 10.00 | −175 | −0.587 | and assume further that sufficient time has occurred for electrode 72 to drift. One may now return electrode 72 to buffer 82 (as shown in FIG. 4B, except that display 18 would now show "4.00", "7.00" and "10.00"). Once key 14G was pressed, "Standardization Values" would now flash; once buffer 82 was recognized as 7.00, "7.00" would begin flashing; once the voltage at jack 30 stabilized, the display at 22 would revert to "7.00" and "7.00" at 18H would stop flashing.

Internally, however, all three standardization values would be updated based upon the measured voltage (once stabilized) with electrode 72 in buffer 82. Assuming that this value is now +1 mV (or the value of voltage divided by temperature is 0.003 mV/deg K. for whatever temperature probe 74 senses in buffer 82), then the value for "7.00" would be updated to 0.003 and the other values also updated as follows:

| pH | mV | mV/deg K |
|---|---|---|
| 4.00 | +179 | 0.600 |
| 7.00 | +1 | 0.003 |
| 10.00 | −176 | −0.591 |

The microprocessor would have measured the change at 7.00 between the old standardization value and the new standardization value (actually the change in mV/deg K.) and applied that change to each of the 4.00 value and the 10.00 value. This recalculation is expressed by the formula:

$$E_{b2} = E_{b1} + (E_{a2} - E_{a1})$$

where $E_{b1}$ is the old value stored at pH 10.00 (or 4.00, if that is being recalculated), $E_{a2}$ is the new value measured at pH 7.00, $E_{a1}$ is the old value stored at pH 7.00 and $E_{b2}$ is the calculated new value at pH 10.00 (or 4.00).

Figure 5:
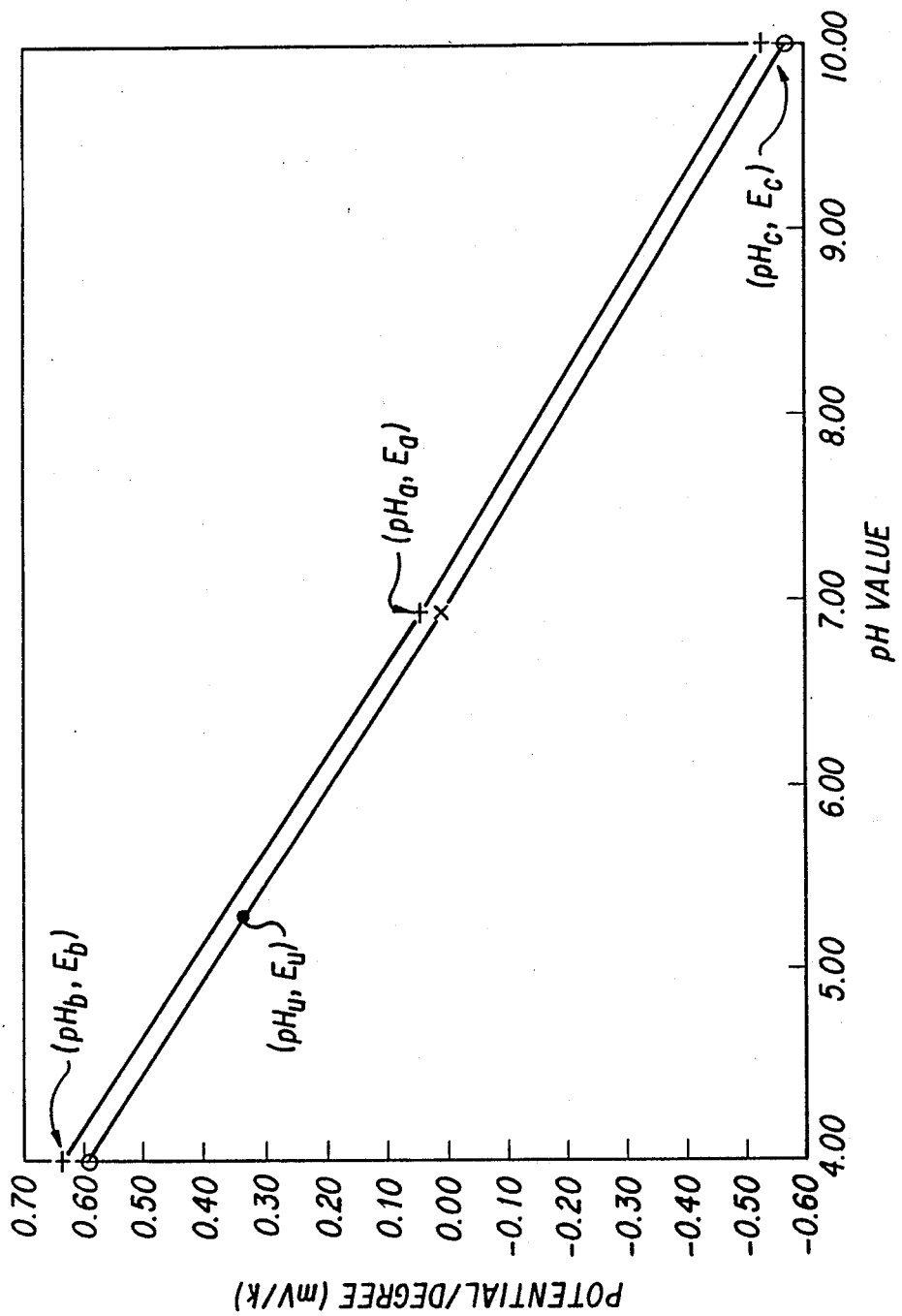
FIG. 5 is a graphic representation of the standardization of the meter of FIG. 1A at three pH values and of the update of such standardization by remeasurement with one standard solution.

FIG. 5 illustrates graphically the three original standardization values (shown by "+" symbols), the newly measured standardization value (shown by a "x" symbol) and the two recalculated standardization values (shown by "o" symbols). The old and new curves show that the effect is to retain the old slope values, but to provide for a new value of the intercept. This type of standardization update recognizes that, given the accepted practise of selecting standard values which tightly "bracket" anticipated unknown values, even if more than two standards are required, drift in slope values has relatively less impact on measurement accuracy than does drift in intercept values. In this context, the drift in electrode slope is relatively slower than the drift in intercept. The effect of drift in slope value would become increasingly large, however, for unknown values significantly outside the standardization range.

If the next update measured −174.0 mV at 15 deg C. in pH 10 buffer [(−174.0/288.16)= −0.604 mV/deg K.], then the stored values would become (4.00, 0.587), (7.00, −0.010) and (10.12, −0.604). The value of 10.12 for the buffer pH is obtained by the ALU referring to a lookup table in ROM in which the non-linear values of buffer pH as a function of temperature are stored.

The actual storage and updating of standardization values in microprocessor 40 (whose components are shown in FIG. 2) is performed in the following manner.

When the pH key 14A is pressed, the ALU 50 sets a flag in RAM 56 indicating the pH mode is in effect. This causes program operation to change to the pH subroutine in ROM 54. The pH subroutine turns on the pH indicator 24 and turns off all other indicators; the following display areas are then blanked: result 22, temperature 20, standard values 18. With the electrode in the first buffer of value pHa, the operator presses Stdz key 14G to initiate the standardization routine. The ALU 50 sets the standardize flag in RAM 56 and program operation is changed to the standardize subroutine in ROM 54. The voltage is read from the pH input 30 into the A/D converter 36, digitized and read by the ALU 50. The ALU stores this number on a five value FIFO stack in RAM 56. The values in the stack are added together and divided by the number of elements that are in the stack to produce a running average. The ALU stores (in RAM 56) and displays (on display area 22) this running average of the input millivoltage from electrode 72. The voltage is then read from the temperature probe 74 into the A/D converter 36, digitized and read by the ALU 50. Utilizing a look up table in ROM 54, the ALU 50 converts this voltage to temperature. The ALU 50 stores this number on a five value FIFO stack in RAM 56. The values in the stack are added together and divided by the number of elements that are in the stack to produce a running average. The ALU 50 displays this running average of temperature in display area 20. Utilizing these two running averages, the ALU 50 determines the buffer value from a table in ROM 54. The ALU 50 then turns on the appropriate buffer indicator in display area 18. This number is flashed on and off every second as determined by timer 52 until both voltage inputs are stable. Stability is determined by the ALU 50 by testing the resolution of the display (from a flag set in RAM 56 in response to closures of the EXP key 14E), and recalling the running average value every second as determined by timer 52 from RAM 56 and testing if the running average has changed by more than the display resolution in the last five seconds as determined by timer 52. If it has, then the test is repeated until there is no further change in the running average to the display resolution. The ALU 50 then divides the pH input voltage running average by the temperature running average and stores this number in RAM 56 as $E_{a1}$. The ALU 50 then sets the buffer value to continuously on in display 18.

As in the case of the first buffer, the meter 10 in like fashion establishes second buffer of value $pH_b$ and the stable $E_b$ value. With the electrode placed in the second buffer of value $pH_b$, the operator presses Stdz key 14G to again initiate the standardization routine. The ALU 50 recalls the values of any prior buffers from RAM 56 and compares them to the current buffer value. If the current buffer value is different than that of $pH_a$, the ALU 50 stores the values $pH_b$ and $E_b$ in RAM 56. If the value of the current buffer were $pH_a$ [the same as the first buffer (e.g, both are pH 10.00)], then the ALU 50 would have stored the current value of $E_a$ in place of the old value of $E_a$.

After a period of use, the electrode 72 is placed back in the first buffer of value $pH_a$ to update the standardizations. The operator presses Stdz key 14G to again initiate the standardization routine. As in the first standardization in first buffer, the meter 10 in like fashion establishes first buffer of value $pH_a$ and the stable E value. The ALU 50 recalls the values of any prior buffers ($pH_a$ and $pH_b$) from RAM 56 and compares them to the current buffer value. Since the value of the current buffer is the same as the first buffer, the ALU 50 stores the values of the current buffer in $pH_a$ and $E_a$ in RAM 56 replacing the previous $E_a$ value. The ALU 50 then gets the value of $E_b$ from RAM 56 and calculates a new $E_b$ value ($E_{b2}$) based on the current and past values of $E_a$ ($E_{a1}$ and $E_{a2}$ respectively) by the formula $E_{b2}=E_{b1}+E_{a2}-E_{a1}$. The ALU 50 then stores this new $E_b$ value in RAM 56, replacing the old $E_b$ value.

The calculation of a pH value (for a sample as illustrated in FIG. 4C) with retained standardization values is performed by the microprocessor 40 as follows. When measuring pH, the ALU 50 inputs, digitizes, maintains a running average and stores the mV and temperature values as illustrated above for standardization. For the purpose of calculating the current pH of the sample, the ALU recalls the standardization values $E_a$, $E_b$, $pH_a$, and $pH_b$ from RAM 56 and then calculates the pH of the unknown ($pH_u$) based upon the equation:

$$pH_u = \frac{[pH_a*(E_u - E_b) - pH_b*(E_u - E_a)]}{E_a - E_b}$$

It will be recognized that this corresponds to the formula for $pX_{u1}$ and $pX_{u2}$ in the Brief Description.

Using the updated standardizations tabulated above, the pH to be displayed when the measured voltage is 0.329 mV/deg K. can be illustrated as follows, referring to the graph of FIG. 5:

$pH_a = 7.00$    $E_{a2} = 0.003$ mV/deg K.
$pH_b = 4.00$    $E_{b2} = 0.600$ mV/deg K.
$pH_u$ to be calculated    $E_u = 0.329$ mV/deg K.

Plugging these values into the above equation yields:

$$\begin{aligned}pH_u &= [7.00(0.329 - 0.600) - 4.00(0.329 - 0.003)]/\\&\quad (0.003 - 0.600)\\&= (-1.897 - 1.304)/(-0.597)\\&= 5.36\end{aligned}$$

If the meter 10 is in the Monitor mode and is reading a sample, the above calculation is performed every one second and the latest result is displayed at display 22 continuously (see FIG. 4C). If the meter 10 is in the Automatic mode, the above calculation is made each one second, but the resultant values are stored in a location in RAM 56, which has space for a fixed number of values (which are retained on a first in/first out basis) in addition to being displayed as in the monitor mode. Once such a value is stored, an average is computed of the fixed number of values (for example, five values). If the latest value remains the same as that average (to the number of decimal places selected with key 14E) for five seconds, then the latest value is displayed on display 22 and the bar 23 stops flashing, as described above in relation to FIG. 4C.

In each one second interval, both potential and temperature are measured For example, assume that the following values are successively calculated by the above formula (the moving average of the five latest values are shown in the second column for mV and in the fourth column for deg K.):

| Latest (mV) | Average (mV) | Latest Temp. (C.) | Average Temp. (C.) | E (mV/degK) | pH |
|---|---|---|---|---|---|
| 180.00 | 180.00 | 25.10 | 25.10 | 0.60 | 3.99 |
| 150.40 | 165.20 | 25.20 | 25.15 | 0.55 | 4.243 |
| 135.60 | 155.33 | 25.10 | 25.13 | 0.52 | 4.408 |
| 122.50 | 147.13 | 25.10 | 25.13 | 0.49 | 4.545 |
| 118.90 | 141.48 | 25.00 | 25.10 | 0.47 | 4.639 |
| 115.70 | 128.62 | 25.00 | 25.08 | 0.43 | 4.853 |
| 114.50 | 121.44 | 25.00 | 25.04 | 0.41 | 4.973 |
| 114.20 | 117.16 | 25.00 | 25.02 | 0.39 | 5.044 |
| 114.05 | 115.47 | 25.00 | 25.00 | 0.39 | 5.072 |
| 114.02 | 114.49 | 25.00 | 25.00 | 0.38 | 5.088 |
| 114.01 | 114.16 | 25.00 | 25.00 | 0.38 | 5.094 |
| 114.00 | 114.06 | 25.00 | 25.00 | 0.38 | 5.096 |
| 114.00 | 114.02 | 25.00 | 25.00 | 0.38 | 5.096 y |
| 114.00 | 114.01 | 25.00 | 25.00 | 0.38 | 5.097 |
| 114.00 | 114.00 | 25.00 | 25.00 | 0.38 | 5.097 * |
| 114.00 | 114.00 | 25.00 | 25.00 | 0.38 | 5.097 x |
| 114.00 | 114.00 | 25.00 | 25.00 | 0.38 | 5.097 |
| 114.00 | 114.00 | 25.00 | 25.00 | 0.38 | 5.097 |
| 114.00 | 114.00 | 25.00 | 25.00 | 0.38 | 5.097 |
| 114.00 | 114.00 | 25.00 | 25.00 | 0.38 | 5.097 |

No matter what resolution was selected, the first thirteen values would not meet the acceptance criterion. If the meter 10 was set for tenths, however, acceptance would occur when the latest reading was 114.00 mV and the running average was 114.02 (designated "y", above; display 22 would then show "5.1", rounding 5.096). If the meter 10 was set for hundredths, acceptance would occur with the latest value at 114.00 and the running average at 114.00 (designated "*" above; display 22 would then show "5.10", rounding 5.097). If the meter 10 was set for thousandths, however, acceptance would not occur until both latest value and running average reached 114.00 for 5 consecutive one second readings (designated "x" above).

Once such a stable value was achieved, the meter in the Automatic mode would stop recalculating the average values of mV or deg K. until key 14D was again pressed. In the Monitor mode, these values would continue to be calculated and the running average values of pH would continue to be displayed.

In similar fashion, voltages and temperatures measured each 0.1 second in a standardization operation would be stored and compared to the latest average of each. The display resolution selected would determine the acceptance criteria for mV and temperature as above for pH measurement.

One can also test the slope of the curve at this point by pressing key 14F which is labeled "Slope". The ALU 50 will now perform a calculation with the values in RAM for $pH_a$, $E_a$, $pH_b$ and $E_b$:

$$\text{Slope} = [298.16(E_a - E_b)]/(pH_b - pH_a)$$

to determine and display on display 22 the slope of the pH versus mV curve at standard temperature of 25 deg C. (298.16 deg K.). It should be noted, however, that slope as such is never used by meter 10 for performing any calculations; instead the stored number pairs ($pH_a$, $E_a$), ($pH_b$, $E_b$) and ($pH_c$, $E_c$) are used. If the incoming potential was above 0.600 mV/deg K., then pressing Slope key 14F would cause the slope between pH 7.00 and pH 10.00 to be calculated.

Returning, now, to the testing of meter 10 with control circuits, as illustrated in FIGS. 3A and 3B, the microprocessor 40 would receive the voltage difference between line 62 and line 60 (V1 measured as in FIG. 3A, V2 measured as in FIG. 3B) as an analog input 32 (see FIG. 1B) converted to a digitized input 36 by A/D Converter 34. The subroutine would cause the ALU 50 to measure and store V1 and measure and store V2. V1 and V2 values would be stored only if they have stabilized (on a running average basis to 0.1 mV) for five seconds. The ALU 50 would then compare V1 to V2 (calculate V1−V2) and compare V1−V2 to the acceptance criterion (e.g., 5 mV). If the criterion is not passed, the ALU 50 causes "Err 7" to be displayed at display 22 and the meter 10 is rejected (if quality control), or is designated for repair or replacement (if use or service testing). The exact duplicate of this procedure is then performed on the ion channel with the rejection message being "Err 8" on display 22.

The operation of meter 10 in the mV mode is simpler than the above operation in the pH mode. Thus, referring to FIGS. 1A and 3A, if meter is turned on and key 14B is pressed, display 22 will merely display the mV value obtained and display 20 will display the temperature sensed (if any probe is connected, otherwise the temperature display 20 will be blank).

The operation of meter 10 in the Ion mode is somewhat similar to operation in the pH mode. Once this mode has been selected by pressing key 14C (see FIG. 1A), the meter should be standardized at two or three of the values available on the top or bottom row of display 18. One selects a standardization value by pressing key 14G; holding 14G causes the values at display 18 to appear in sequence, "1.0", then "2.5" through to "1000" and then back to "1.0". When pressure is removed from key 14G, display 18 stops changing and the meter is ready to standardize (a pX electrode should by then be connected to jack 31 and immersed in a standard solution having the corresponding value of the ion X. Thus, for example, a sodium electrode might be standardized at 50.0, 100 and 500 ppm or a fluoride electrode might be standardized at 2.5, 5.0 and 10.0 ppm. The sequence of flashing displays and displayed values at 22 will be similar in each case to the standardization of pH described above except that the meter 10 does not search memory to recognize which standard is being used (and hence "Standardization Values" does not flash in display 18, only the numeral in display 18 which was selected with key 14G).

The actual values stored in RAM during this standardization operation in the Ion Mode are preferably also indicative of mV/deg K. at each standardization level. Assuming that all three standardizations are performed at 25 deg C., the following illustrate typical standardizations for a sodium electrode (with its reference electrode) and for a fluoride electrode (with its reference electrode):

| Standardization | mV | mV/deg K | -pX |
|---|---|---|---|
| For Sodium | | | |
| 50.0 | −12.0 | −0.040 | 1.69897 |
| 100 | +7.0 | +0.023 | 2.00 |
| 500 | +45.0 | +0.151 | 2.69897 |
| For Fluoride | | | |
| 2.5 | +233.0 | 0.781 | 0.39794 |
| 5.0 | +217.0 | 0.728 | 0.69897 |
| 10.0 | +197.0 | 0.661 | 1.0000 |

As with standardizations in the pH mode, these standardizations can be updated with a single measurement. Assume, for example, that the meter 10 has the above three standardization values for fluoride and has been used for a series of fluoride determinations for a sufficiently long period for drift to have occurred. Now the electrode pair is immersed in a 5.0 standard at 25 deg C. and key 14G is used to select "5.0" on display 18. Assume further that two significant figures has been selected with the expansion key 14E. The numeral "5.0" will flash at 18C in display 18 until the latest voltage at jack 31 is within 0.3 mV of the weighted average of the last five values for five seconds while the actual potential (e.g., 220 mV) is displayed at display 22. Once that criterion is met (a criterion of 0.1 mV instead of 0.3 mV is used if three significant figures has been selected with expansion key 14E), "5.0" remains displayed at 18C, the display 22 shows "5.0", and the Standardization Values stored in RAM become:

| Standardization | mV/deg K | -pX |
|---|---|---|
| 2.5 | 0.791 | 0.39794 |
| 5.0 | 0.738 | 0.69897 |
| 10.0 | 0.671 | 1.0000 |

It can be seen that the standardization for 2.5 and 10.0 have been increased by 0.010 mV/deg K., which corresponds to the difference between the new value at "5.0" compared to the old value at "5.0".

In computing ion concentrations of unknown samples, the above table corresponds to the stored values for ($pX_a$, $E_a$), ($pX_b$, $E_b$) and ($pX_c$, $E_c$) of (0.39794, 0.791), (0.69897, 0.738) and (1.0000, 0.671). The pX values are stored as positive rather than negative numbers for convenience. Once the $pX_u$ value for the unknown solution is calculated from two of these three stored value pairs and from $E_u$, it is converted by ALU 50 to a concentration value (in whatever concentration units were used for the standards), which is displayed at display 22.

We claim:

1. A method for measuring pX values in unknown solutions with calibration comprising the steps:
    (a) measuring the voltage output of an electrode pair in a first solution of known pX value ($pX_a$) and storing this value as $E_{a1}$;
    (b) measuring the voltage output of the electrode pair in a second solution of known pX value ($pX_b$) and storing this value as $E_{b1}$;
    (c) thereafter measuring the voltage output of the electrode pair in a first solution of unknown pX ($pX_{u1}$) and computing $pX_{u1}$ according to the formula:

$$pX_{u1} = \frac{pX_a{}^*(E_{u1} - E_{b1}) - pX_b{}^*(E_{u1} - E_{a1})}{E_{a1} - E_{b1}}$$

and reporting the computed value of $pX_{u1}$;
    (d) thereafter remeasuring the voltage output of the electrode pair in a solution of the first known pX value $pX_a$ and storing the remeasured value $E_{a2}$;
    (e) thereafter changing the stored value $E_{b1}$ to a stored value $E_{b2}$ according to the formula:

$$E_{b2} = E_{b1} + (E_{a2} - E_{a1});$$

and
    (f) thereafter measuring the output voltage $E_{u2}$ of the electrode pair in a second solution of unknown pX and computing $pX_{u2}$ according to the formula:

$$pX_{u2} = \frac{pX_a{}^*(E_{u2} - E_{b2}) - pX_b{}^*(E_{u2} - E_{a2})}{E_{a2} - E_{b2}}$$

and reporting the computed value of $pX_{u2}$.

2. The method of claim 1 wherein, during the measuring step (b), the thereafter measuring step (c) and the thereafter remeasuring step (d), the temperature of the solution being measured is also measured, and wherein the stored values $E_{a1}$, $E_{b1}$ and $E_{a2}$ and the calculated value $E_{b2}$ are all in units of potential/temperature, wherein temperature is expressed on a basis wherein absolute zero is 0.

3. The method of claim 2 wherein, during each step of measuring a solution of unknown pX (steps (c) and (f)), the temperature of the solution of unknown pX is also measured, and wherein $E_{u1}$ is also expressed in units of potential/temperature in the formula for calculating $pX_{u1}$.

4. The method of claim 1 wherein the first and second solutions of known pX value are each pH standard solutions and wherein the first and second solutions of unknown pX are solutions of unknown pH.

5. The method of claim 4 further comprising measuring the voltage output of the electrode pair in a third solution of known pH value ($pH_c$) and storing this value as $E_{c1}$ prior to the remeasuring step (d), and, after the remeasuring step (d) changing the stored value $E_{c1}$ to a stored value $E_{c2}$ according to the formula:

$$E_{c2} = E_{c1} + (E_{a2} - E_{a1}).$$

6. The method of claim 5 wherein the temperature of the solution of known pH is measured during each of the measuring steps thereon, wherein the stored values $E_{a1}$, $E_{b1}$, $E_{c1}$ and $E_{a2}$ and the calculated values $E_{b2}$ and $E_{c2}$ are each in units of potential/temperature, with temperature being expressed on a basis wherein absolute zero is 0.

7. The method of claim 6 wherein, for each subsequent unknown sample, the pH is calculated according to one of the following formulae:

$$pH_u = \frac{pH_a{}^*(E_u - E_{b2}) - pH_b{}^*(E_u - E_{a2})}{E_{a2} - E_{b2}}$$

or $$pH_u = pH_a{}^* \frac{(E_u - E_{c2}) - pH_c{}^*(E_u - E_{a2})}{E_{a2} - E_{c2}}$$

or $$pH_u = pH_b{}^* \frac{(E_u - E_{c2}) - pH_c{}^*(E_u - E_{b2})}{E_{b2} - E_{c2}}$$

wherein $E_u$ is potential/temperature measured for the sample, wherein $pH_a$, $pH_b$ and $pH_c$ are the standard pH values of the first, second and third solutions of known pH.

8. The method of claim 7 wherein, if $E_u$ is more than one or two of $E_{a2}$, $E_{b2}$ and $E_{c2}$ and is less than two or one of $E_{a2}$, $E_{b2}$ and $E_{c2}$, then that formula for $pH_u$ is employed which contains the two values among $E_{a2}$, $E_{b2}$ and $E_{c2}$ which are next lower than $E_u$ and which are next higher than $E_u$; but if $E_u$ is either higher or lower than all of $E_{a2}$, $E_{b2}$ and $E_{c2}$, then that formula for $pH_u$ is employed which contains the two values among $E_{a2}$, $E_{b2}$ and $E_{c2}$ which are closest to $E_u$.

9. The method of claim 1 wherein the first and second solutions of known pX are of known concentration of an ion other than hydronium and wherein the first and second solutions of unknown pX are of unknown concentrations of the ion, and wherein the ion concentrations are stored and calculated as $pX_u$ values and are calculated and displayed as $X_u$ values, based upon the formula:

$$X_u = 10^{-pX_u}.$$

10. The method of claim 1 wherein the voltage output of the electrode and a voltage output of a temperature probe are each periodically measured, and wherein a running average of a fixed number of latest values of each is computed; and wherein the latest value of each is compared to the corresponding latest running average to determine when a stable electrode potential and a stable temperature measurement have been achieved.

11. A meter having means for receiving the voltage output of an electrode pair, means for storing standard voltages ($E_{a1}$ and $E_{b1}$) from the immersion of the electrode pair into standard solutions, means for calculating the pX value of an unknown solution ($pX_{u1}$) from the measured value $E_{u1}$ and the stored standard values, means for updating $E_{a1}$ to $E_{a2}$ upon remeasuring the voltage output of an electrode pair in a standard of a first known pX ($pX_a$), means for updating another stored standard voltage ($E_{b1}$ to $E_{b2}$) without remeasurement by the formula:

$$E_{b2} = E_{b1} + (E_{a2} - E_{a1})$$

and means for computing the pX value of a second unknown solution from the measured voltage output of the electrode pair in an unknown solution $E_{u2}$ and from the updated standard values $E_{a2}$ and $E_{b2}$.

12. The meter of claim 11 further comprising means for storing a third standard voltage $E_{c1}$ and means for updating $E_{c1}$ to $E_{c2}$ without remeasurement by the formula:

$$E_{c2}=E_{c1}+(E_{a2}-E_{a1}).$$

13. The meter of claim 12 wherein the meter further comprises means for receiving a value of temperature as each standard solution is being measured, and wherein each of $E_{a1}$, $E_{a2}$, $E_{b1}$, $E_{b2}$, $E_{c1}$ and $E_{c2}$ is stored in units of potential/temperature, with temperature being expressed on a basis wherein absolute zero is 0.

14. A method for testing a pH or pX meter for excessive internal voltage which comprises the steps:
 (a) connecting the electrode inputs of the meter to an external circuit having a known voltage of value E1 and a low external resistance and storing the measured voltage V1,
 (b) connecting the electrode inputs of the meter to an external circuit having the known voltage E1 and a large known resistance R1 and storing the measured voltage V2,
 (c) having the meter calculate the value of the difference between V1 and V2,
 (d) having the meter compare the calculated difference to a permitted range which is preset in he meter and is based upon fixed values of E1 and R1, and
 (e) if the difference between V1 and V2 is outside the preset limits, having the meter display an error mesage indicating that the meter is out of specification.

15. The method of claim 14 wherein V1 and V2 are stored by the meter in steps (c) and (d).

16. The method of claim 14 wherein, during step (a), a running average of V1 values is calculated and V1 is stored once the running average remains equal to the latest V1 value for a fixed time period, and wherein, during step (b), a running average of V2 values is calculated and V2 is stored and used to calculate a difference once the running average remains equal to the latest V2 value for a fixed period of time.

* * * * *